United States Patent [19]
Phillips et al.

[11] Patent Number: 5,376,066
[45] Date of Patent: Dec. 27, 1994

[54] GLOVE FOR THE TREATMENT AND/OR PREVENTION OF CARPAL TUNNEL SYNDROME

[76] Inventors: Timothy W. Phillips, 131 Branford Pl.; William C. Childers, 153 West Lake Ct., both of Athens, Ga. 30606

[21] Appl. No.: 71,808

[22] Filed: Jun. 2, 1993

[51] Int. Cl.$^5$ ............................................. A61F 5/00
[52] U.S. Cl. ...................................... 602/21; 602/64; 2/16
[58] Field of Search .................................. 602/20–22, 602/60–64, 75–77; 2/161.1, 16

[56] References Cited

U.S. PATENT DOCUMENTS

| | | | |
|---|---|---|---|
| 3,327,703 | 6/1967 | Gamm | 602/21 |
| 3,997,922 | 12/1976 | Huhta | 2/161.1 |
| 4,546,495 | 10/1985 | Castillo | 2/161.1 |
| 4,632,106 | 12/1986 | Gamm | 602/63 |
| 4,765,319 | 8/1988 | Finnieston et al. | 602/21 |
| 4,832,010 | 5/1989 | Lerman | 602/65 X |
| 4,850,341 | 7/1989 | Fabrey et al. | |
| 4,854,309 | 8/1989 | Elsey | |
| 4,941,460 | 7/1990 | Working | |
| 5,014,689 | 5/1991 | Meunchen et al. | |
| 5,092,318 | 3/1992 | More et al. | 602/63 X |
| 5,160,314 | 11/1992 | Peters | |

*Primary Examiner*—Richard J. Apley
*Assistant Examiner*—Linda C. M. Dvorak
*Attorney, Agent, or Firm*—Caesar, Rivise, Bernstein, Cohen & Pokotilow, Ltd.

[57] ABSTRACT

A glove-like device to be worn on the hand and wrist of a person to prevent or treat carpal tunnel syndrome. The device is a sleeve formed of an elastic material, e.g., neoprene, which stretches longitudinally as well as transversely and includes a palmar side, a dorsal side, a distal end portion, an intermediate portion, and a proximal end portion. The distal end portion of the sleeve includes respective finger receiving openings. A thumb receiving opening is provided in the intermediate portion of the sleeve. The proximal end of the sleeve includes a releasably securable strap located adjacent the wrist of the person for wrapping about a portion of the wrist to secure the glove-like device in place. When the device is in place the person's fingers extend through the respective finger openings and the person's thumb extends through the thumb opening. The dorsal side of the sleeve is biased backward for extending the person's hand in flexion at a slight angle, e.g., 25–30 degrees, to the wrist axis so that it is in a neutral position. The intermediate portion of the sleeve is configured to tightly encircle the palm and contiguous dorsal portion of the hand to resist the palm from spreading. A pad may be provided on the palmar side of the glove-like member at the interface of the intermediate portion and proximal end portion.

9 Claims, 4 Drawing Sheets

GLOVE FOR THE TREATMENT AND/OR PREVENTION OF CARPAL TUNNEL SYNDROME

SPECIFICATION

This invention relates generally to orthopedic devices, and more particularly to gloves for treating and/or preventing carpal tunnel syndrome in persons.

BACKGROUND OF THE INVENTION

Various types of braces, supports, or glove-like devices are disclosed in the patent literature and are commercially available for treating or preventing carpal tunnel syndrome. Examples of such prior art devices are shown in the following U.S. Pat. Nos.: 4,850,341 (Fabry et al.), 4,854,309 (Elsey), 4,941,460 (Working), 5,014,689 (Meunchen et al.), and 5,160,314 (Peters).

While the aforementioned devices are a step in the right direction toward the treatment and prevention of carpal tunnel syndrome, they still leave much to be desired from one or more of the following standpoints, effectiveness, non-interference with normal motion, comfort, and ease and simplicity of application and removal.

OBJECTS OF THE INVENTION

Accordingly, it is the general object of this invention to provide a glove-like device for which overcomes the disadvantages of the prior art.

It is a further object of this invention to provide a glove-like device which serves to treat or prevent the occurrence of carpal tunnel syndrome in persons wearing the device.

It is another object of this invention to provide a glove-like device which for treating or preventing the occurrence of carpal tunnel syndrome, yet which does not immobilize the hand and wrist of the wearer or otherwise hinder or impede normal motion of the hand and wrist.

SUMMARY OF THE INVENTION

These and other objects of the instant invention are achieved by providing a glove-like device and method of use so that it may be worn on a person's hand and over a portion of the person's wrist to prevent or treat carpal tunnel syndrome.

The device basically comprises a sleeve of elastic material, e.g., fabric covered neoprene, which stretches longitudinally as well as transversely and which includes a palmar side and a dorsal side, a distal end portion, an intermediate portion, and a proximal end portion. The distal end portion includes plural respective finger receiving openings. The intermediate portion of the sleeve includes a thumb receiving opening. The proximal end portion of said sleeve is configured to encircle the wrist of the person when the device is in place with the person's fingers extending through the respective finger openings and with the person's thumb extending through the thumb opening.

In accordance with one aspect of this invention the dorsal side of said sleeve is biased backwards at a slight angle, e.g., 5 or 6 degree, to the axis of the person's wrist for extending the person's hand in flexion at that slight angle to that axis.

In accordance with another aspect of this invention the intermediate portion of the sleeve is configured to tightly encircle the person's palm and contiguous dorsal portion of the person's hand to prevent the palm from spreading.

DESCRIPTION OF THE DRAWINGS

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Figure 1:
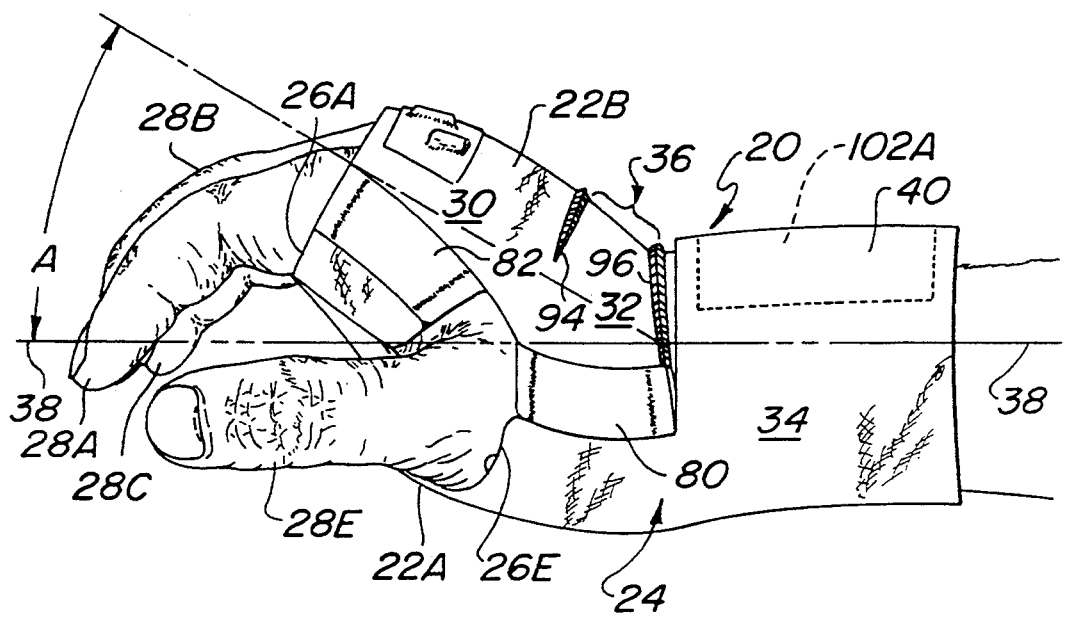
FIG. 1 is a side elevational view of one embodiment of a glove-like device constructed in accordance with the subject invention and shown in place on the hand and wrist of a person.

Referring now in detail to the various figures of the drawing wherein like reference characters refer to like parts, there is shown at 20 in FIG. 1 a glove-like device constructed in accordance with the subject invention for wearing on the hand and wrist of a person at risk to acquire carpal tunnel syndrome from repetitive motion, e.g., typing, to prevent the onset of that syndrome or by a person already afflicted with and suffering from that syndrome to treat it and hasten its resolution. The device 20 is formed from a sheet 22 (FIG. 7) or blank of an elastic material which stretches longitudinally as well as transversely. The sheet 22 of material is cut in accordance with a predetermined pattern, to be described later and is then rolled up, with selected portions of it secured together, e.g., glued and/or sewn, to form a sleeve 24 having plural finger openings 26A, 26B, 26C, and 26D, and a thumb opening 26E. The sleeve is arranged to be worn on the hand and over a portion of the wrist, with the person's "index" finger 28A extending through opening 26A, the "middle" finger 28B extending through opening 26B, the "ring" finger 28C extending through opening 26C, the "little" finger (not shown) extending through opening 26D, and the thumb 28E extending through opening 26E.

It should be pointed out at this juncture that while the glove-like device 20 is shown as being of a finger-less type, in the interests of comfort and/or safety or protection, the device can include finger portions. Examples of applications for which a glove with fingers may be desirable are, applications wherein the weather is cold or wet, and applications wherein the person's fingers may be exposed to injury.

The material making up the sleeve 24 comprises an elastomeric foam, e.g., neoprene rubber, core whose outer surface is covered by fabric, e.g., nylon, and whose inner surface is also covered by a similar fabric. Other materials can be used to make the sleeve. Thus, it is contemplated that the sleeve can be formed of a woven or knitted fabric, so long as a portion of it is elastic in both the longitudinal and transverse directions. In any case the sleeve 22 includes palmar side 22A and a dorsal side 22B, a distal end portion 30, an intermediate portion 32, and a proximal end portion 34. The finger openings 26A-26D are located in the distal end portion of the sleeve, and the thumb opening 26E is located in the intermediate portion of the sleeve at the juncture of the palmar and dorsal sides, 22A and 22B, respectively.

In accordance with one fundamental aspect of this invention, the intermediate portion 32 of the sleeve 22 is configured so that it tightly encircles the person's palm and contiguous dorsal portion of the person's hand to prevent the base of the person's palm from spreading. This action compresses the carpal tunnel, thereby closing it slightly so that the median nerve extending through that tunnel is less vulnerable to injury or strain. The palm compression feature of this invention is of considerable importance to protect the wearer when performing various types of repetitive hand actions, e.g., typing, since such actions typically tend to spread the palm, thereby applying extra strain or pressure on the carpal tunnel.

In accordance with another fundamental aspect of this invention, and as can be seen clearly in FIGS. 1, 2, 3 and 6, the dorsal side 22A of the sleeve 24 is biased backwards by biasing means 36, to be described later, so that the sleeve's proximal end portion 30 and its contiguous intermediate portion 32 extends at a slight angle A, e.g., 25-30 degrees, to the axis 38 of the person's wrist. Thus, when the glove-like device 20 is in place on the person's hand and wrist, the person's hand is extended in flexion at that slight angle to the axis 38 of the wrist. This flexion places and supports the hand in a physiologically desirable "neutral" position which is well suited to enable the person to safely accomplish repeated tasks with his/her hand. Moreover, inasmuch as the glove-like device 20 is formed of an elastic material, as opposed to rigid or splinted devices of the prior art, it allows for some flexibility to enable the wearer to bend or flex his/her wrist to any desired orientation to complete the task at hand, yet it returns the hand to the "neutral" position thereafter.

The proximal end portion 34 of the sleeve 22, includes releasable securement means, in the form of an extendable strap 40 (to be described later), which is configured to encircle a portion of the wrist of the person to hold the clove-like device 20 in place against slippage.

Figure 7:
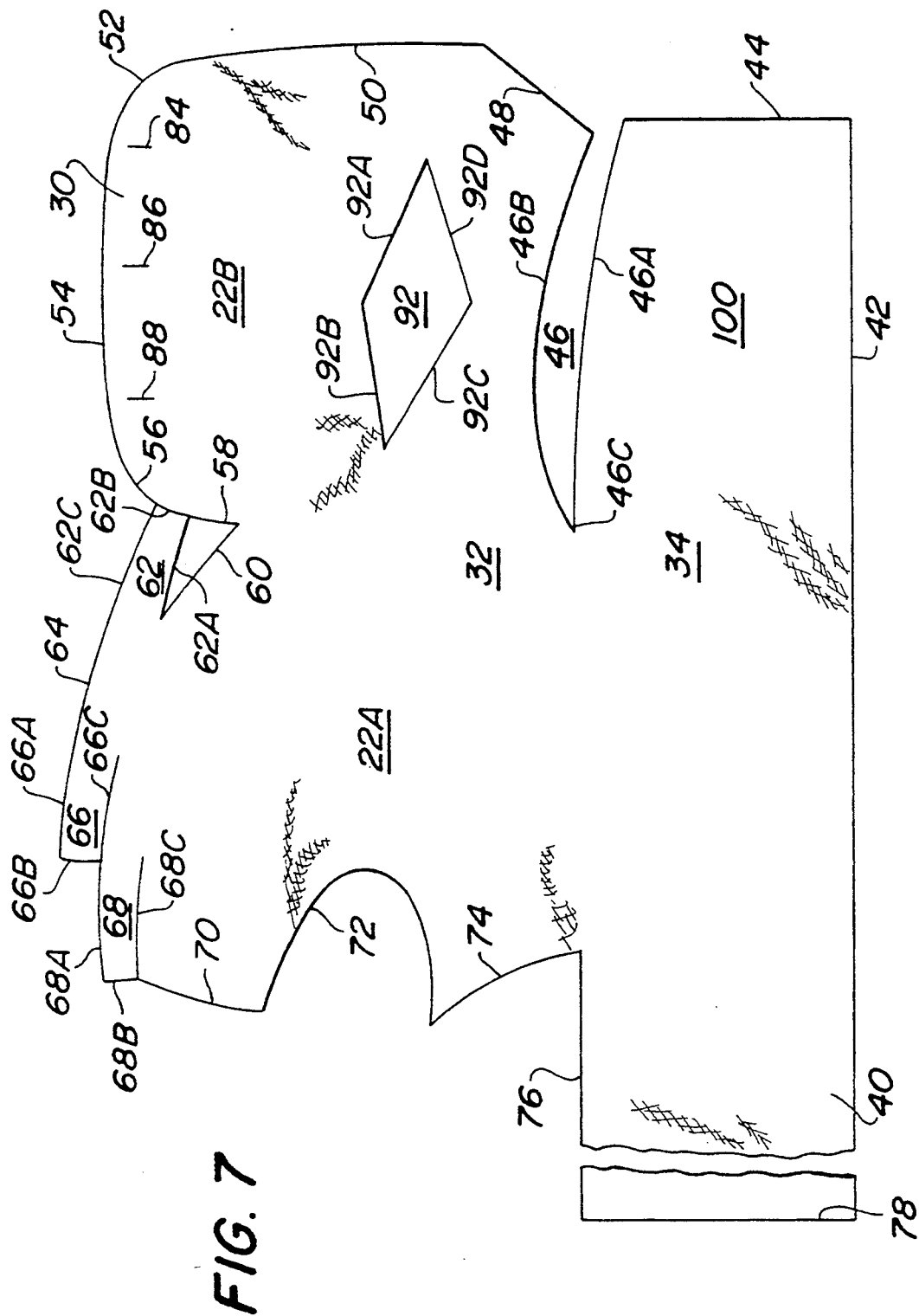
FIG. 7 is a plan view of a blank of elastic material showing the pattern to which it has been cut so that it can be assembled into the embodiments of the devices shown in FIGS. 1 and 5.

Referring now to FIG. 7 it can be seen that the blank 22 of material forming the sleeve 24 is of irregular shape. In particular, the periphery of the blank 22 comprises a linear bottom edge 42, a generally linear side edge 44, a slot 46 in the side edge which is formed by a pair of adjacent arcuate edges 46A and 46B which merge together at an apex point 46C, an angularly extending edge 48, a somewhat linear side edge 50, an arcuate corner edge 52, a somewhat linear top edge 54, an arcuate corner edge 56, a somewhat linear short side edge 58 terminating at an angularly extending edge 60, a tab 62, a generally linear top edge 64, a tab 66, a tab 68, a generally linear short side edge 70, a generally U-shaped concave edge 72, a short and slightly concave side edge 74, a generally linear edge 76, and a generally linear edge 78. The tab 62 is formed by edges 62A, 62B and 62C. The tab 66 is formed by edges 66A, 66B and 66C. The tab 68 is formed by edges 68A, 68B and 68C.

The portion of the blank bounded by the edges 46B, 48, 50, 52, 54, 56, and 58, and the imaginary line connecting the junction of edges 58 and 60 to the apex point 46C of slot 46 defines the heretofore identified dorsal portion 22B of the sleeve. The portion of the blank 22 bounded by the edge 60, the tab 62, the edge 64, the tab 66, the tab 68, the edges 70, 72, 74, 74, and 78, and the imaginary line connecting the junction of edges 58 and 60 to the edge 42 and extending through the apex point 46C of slot 46 defines the heretofore identified palmar portion 22A of the sleeve. The sleeve is assembled by gluing and stitching the edges 46A and 46B of the slot 46 together. The blank forming the sleeve is rolled up so that the edge 48 abuts the edge 74. The abutting edges are glued together and a strip 80 (FIGS. 1, 2, 4 and 5) of longitudinally stretchable elastic is disposed over the glued joint and is stitched in place to reinforce that joint. The edge 70 is also brought into abutment with the portion of the edge 50 contiguous with the corner edge 52, and those abutting edges are glued together. A strip 82 (FIGS. 1, 2 and 5) also of longitudinally stretchable elastic is disposed over the glued joint and is stitched in place to reinforce that joint.

The peripheral edges 48, 50, 72 and 74 of the blank 22 define what can be called a progressive compression contour at the intermediate portion 32 of the sleeve when the sleeve is assembled. In particular, the intermediate portion is configured so that it will tightly encircle the palm and contiguous dorsal portion of the wearer's hand when the sleeve is in place, thereby applying a compressive force to the palm to prevent it from spreading. In accordance with one aspect of this invention the progressive compression is isolated to the portion of the hand where it is needed, namely, the base of the palm, thereby resulting in a device which is effective, yet comfortable, e.g., non-cramping. The glove like device may be made in various sizes, e.g., small, medium and large, with proportional progressive contouring to accommodate various sized hands.

Figure 4:
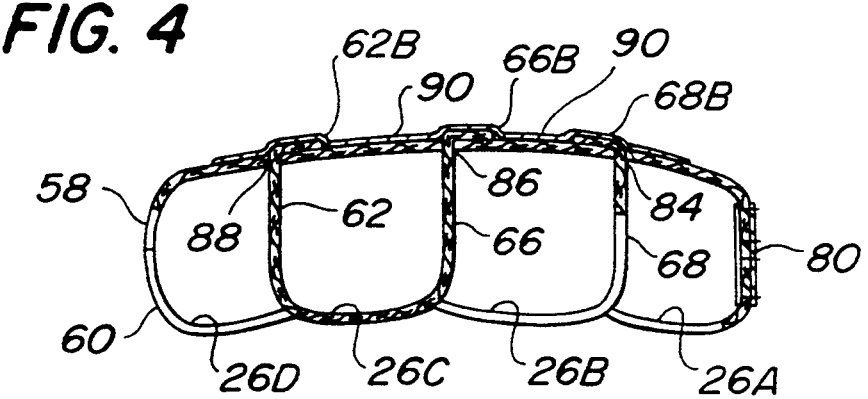
FIG. 4 is a sectional view taken along line 4—4 of FIG. 3.

As can be seen clearly in FIGS. 2 and 4 the tab 68 is bent out of the plane of the blank 22 and its free end edge 68B is extended through a slit 84 (FIGS. 4 and 7) in the portion of the blank directly below the top edge 54 of the dorsal side so that tab forms the finger hole 26A. In a similar manner the tab 66 is bent out of the plane of the blank and its free end edge 66B is extended through a respective slit 86 (FIGS. 4 and 7) in the portion of the blank below the top edge 54 of the dorsal side to form the finger hole 26B, and the tab 62 is bent out of the plane of the blank and its free end is extended through a respective slit 88 in the portion of the blank below the top edge 54 of the dorsal side to form the finger hole 26C. The finger hole 26D is formed between the tab 62 and the adjacent edges 58 and 60. The free ends of the tabs which extend through the slits 84, 86, and 88 are glued in place and covered by a strip 90 (FIGS. 2 and 4) of elastic fabric adhesively secured thereover. When the sleeve is assembled as just described the concave edge 70 and the adjacent portion of the edge 50 create the heretofore identified thumb hole 26E.

Figure 2:
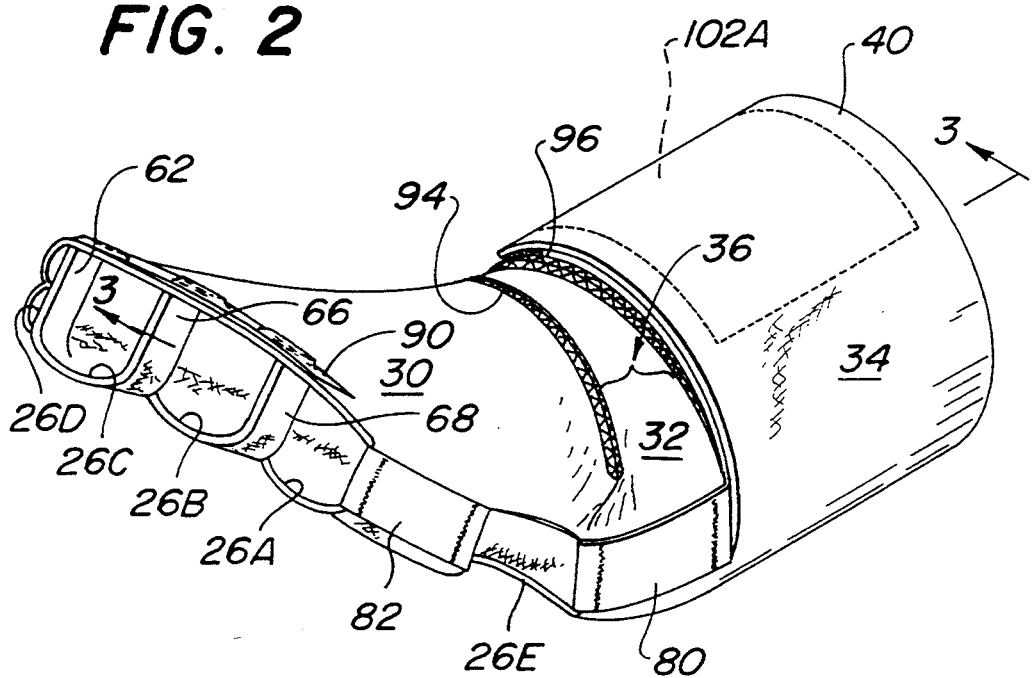
FIG. 2 is an isometric view of the glove-like device shown in FIG. 1.
Figure 3:
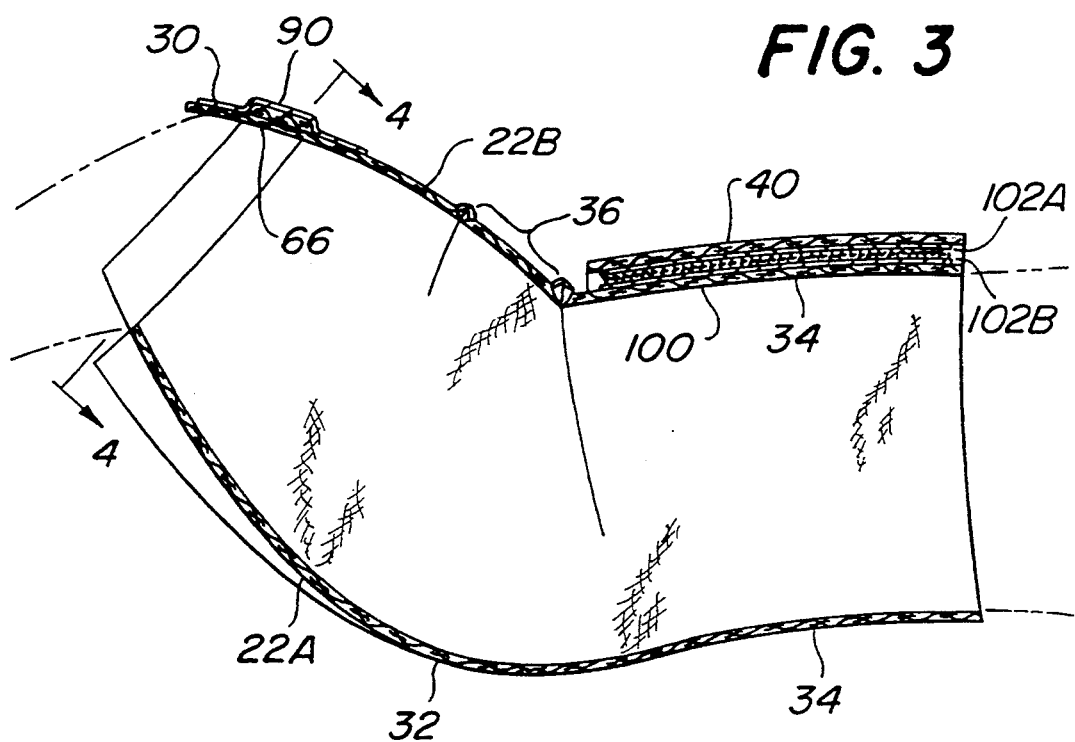
FIG. 3 is a sectional view taken along line 3—3 of FIG. 2.

Referring now to FIGS. 1, 2, and 7, the details of the biasing means 36 for the sleeve 24 will now be described. The biasing means basically comprises a pair of joint or seam lines 94 and 96 which serve to provide tension in the longitudinal direction, i.e., parallel to axis 38, along the dorsal side 22B of the sleeve, to thereby cause the distal end portion 30 and contiguous intermediate portion 32 of the sleeve to extend backward at the slight angle A, e.g., 25–30 degrees, to the axis 38. The seam line 96 is formed when the edges 46A and 46B of the slot 46 are secured to each other, as described earlier. The seam line 94 starts out as a diamond shaped opening 92 (FIG. 7) in the blank 22 forming the sleeve and is closed to form the seam line 94 by bringing the peripheral edges of the opening into abutment.

The triangular shaped opening 92 comprises four sides, 92A, 92B, 92C, and 92D, with the juncture of the sides 92A and 92D forming one end of the major axis of the opening 92 and the juncture of the sides the 92B and 92C forming the other end of that axis. The juncture of the sides 92A and 92B form one end of the minor axis of the opening 92, while the juncture of the sides the 92C and 92D form the other end of that axis. The minor axis of the opening 92 extends generally parallel to the longitudinal axis of the sleeve (and also to the axis 38), while the major axis extends generally transversely of the sleeve. The opening 92 is closed by bringing the edges 92A and 92D into abutment and by bringing the edges 92B and 92C into abutment, thereby closing the opening along its major axis. The closed opening is sealed by gluing and stitching the abutting edges together to form the seam line 94.

As should be appreciated by those skilled in the art the formation of the seam lines 94 and 96 apply tension longitudinally to the material making up the dorsal side of the sleeve, thereby causing the sleeve to assume the angled orientation described above. Moreover, the seam lines 94 and 96 resist stretching along their length, which is in the transverse direction of the sleeve. This action accentuates the compression applied to the palm by the encircling intermediate portion of the sleeve.

Figure 5:
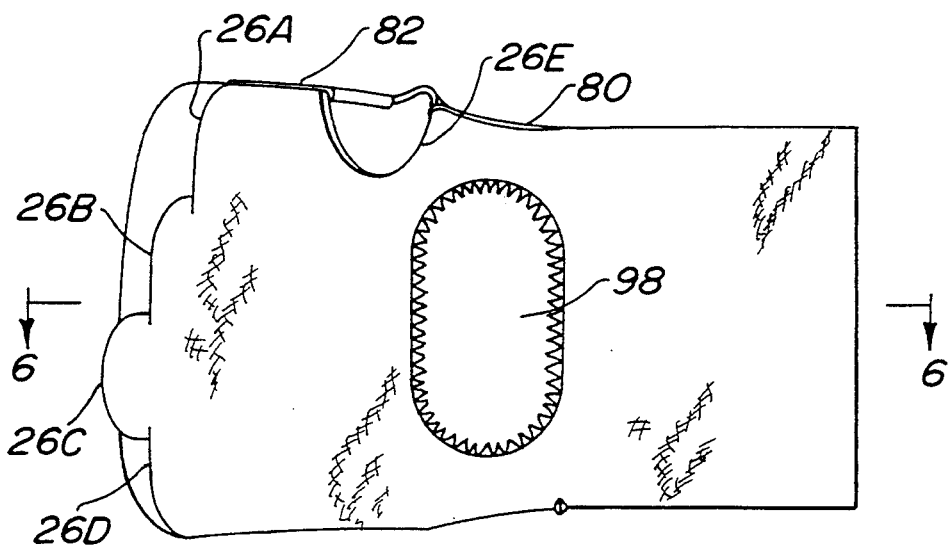
FIG. 5 is a plan view of the palmer side of an alternative embodiment of a glove-like device constructed in accordance with this invention.
Figure 6:
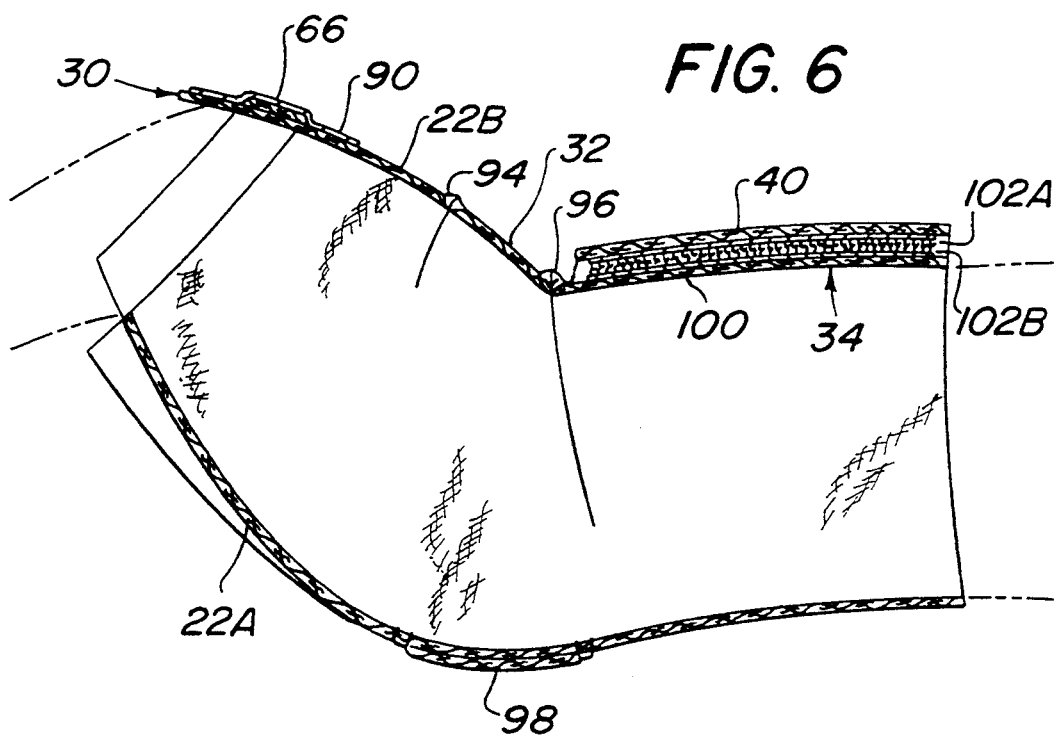
FIG. 6 is an enlarged sectional view taken along line 6—6 of FIG. 5.

In some applications it may be desirable to provide a shock or impact absorbing pad across the base of the palm for added protection. This arrangement is shown in the embodiment of FIG. 5. To that end a flat oval shaped pad 98, formed of any suitable material, e.g., fabric covered neoprene rubber, is glued and sewn onto the palmar side of the intermediate portion 34 of the sleeve located just proximally of the thumb hole 26E. The pad preferably extends across the entire base of the palm and is reinforced with peripheral stitching. If desired a small heat-moldable, plastic insert (not shown) just slightly smaller than the pad 98 may be interposed in a pocket (not shown) formed between the pad 98 and the underlying portion of the sleeve for added protection. That arrangement, by overlapping the outside edge of the hand across the base of the palm, acts as additional reinforcement to prevent palm spread.

Attention will now be directed to FIGS. 1, 2, 3, 6, and 7 wherein the details of the releasable securement strap 40 and its associated components will be described. Thus, as can be seen therein the strap 40 is formed by the portion of the blank 22 which is bounded by the edges 76, 78, and a portion of the edge 42 located under the juncture of edges 74 and 76. When the sleeve is assembled the strap 40 will thus extend laterally outward from the distal end portion of the sleeve. The strap 40 is arranged to be wrapped around a portion of the wearer's wrist when the sleeve is in place so that the free end of the strap 40 overlies and is releasably secured to a section 100 of the proximal end portion 34 of the sleeve, whereupon the entire wrist and contiguous portion of the wearer's forearm are encircled. This action secures the device in place against sliding.

The means for releasably securing the strap 40 to the underlying proximal end portion of the sleeve comprises a VELCRO fastening system. In particular a patch 102A of the loop component of a VELCRO fastening system is adhesively secured and sewn onto inner surface of the strap, while a patch 102B of hook component of that fastening system is adhesively secured and sewn onto the outer surface of the section 100 of the proximal end portion 34 of the sleeve. Accordingly, when the strap 40 is wrapped around the wearer's wrist like shown in FIGS. 1–3, the two patches 102A and 102B releasably engage each other to secure the strap in place against dislodgement.

It should be pointed out at this juncture that the sleeve can be formed of a unitary blank 22 of material, as described above, or can be formed of plural sections which are secured together. For example, the dorsal side 22A portion can be one section, and the palmar side portion and strap 40 can be another section. This alternative construction may be desirable if the sleeve is to be formed of an elastic material other than neoprene rubber, e.g., an elastic mesh for a "cooler" wearing glove. In fact, the entire glove-like device need not be elastic. Thus, the glove may be formed of an inelastic material, so long as its intermediate portion is elastic to provide the compression at the base of the palm. Moreover, the opening 92 need not be triangular, e.g., it may be oval, so long as it serves to pull the dorsal side of the sleeve backward when it is closed. In fact, other means than the seam lines described heretofore can be used to bias the sleeve in the desired orientation.

Without further elaboration, the foregoing will so fully illustrate our invention that others may, by applying current or future knowledge, readily adopt the same for use under various conditions of service.

We claim:

1. A device to be worn on the hand and over a portion of the wrist of a person to prevent or treat carpal tunnel syndrome, said device comprising of a sleeve of elastic material which stretches longitudinally as well as transversely and which includes a palmar side and a dorsal side, a distal end portion, an intermediate portion, and a proximal end portion, said distal end portion including plural respective finger receiving openings, said sleeve having a thumb receiving opening located in said intermediate portion, said proximal end portion of said sleeve having a longitudinal axis and being configured to encircle the wrist of the person when said device is in place with the person's fingers extending through said respective finger openings and with the person's thumb extending through said thumb opening, said dorsal side of said sleeve at said intermediate portion being formed of a blank of said elastic material having a hole therein., said hole having peripheral edge portions spaced apart from each other and being permanently closed by bringing said peripheral edge portions into abutment with each other, whereupon said dorsal portion of said sleeve is biased backwards at a slight angle to said longitudinal axis for extending the person's hand in flexion at said slight angle to said longitudinal axis, said dorsal side of said sleeve also including a slot therein located adjacent said closed hole, said slot having peripheral edge portions spaced apart from each other, said slot being permanently closed by bringing said peripheral edge portions of said slot into abutment with each other to further the biasing of said dorsal side of said sleeve backwards, said intermediate portion of said sleeve being configured to tightly encircle the person's palm and contiguous dorsal portion of the person's hand to prevent the palm from spreading.

2. The device of claim 1 additionally comprising said releasably securable means located at said dorsal portion of said sleeve, said releasably securable means comprises a first portion of said dorsal side of said sleeve at said proximal end portion, a second portion of said palmar side of said sleeve at said proximal end portion, a strap portion projecting from said second portion, and fastening means, said strap portion being arranged to be extended over said first portion and releasably secured thereto by said fastening means.

3. The device of claim 2 wherein said fastening means comprises a two component, hook and loop fastening system.

4. The device of claim 3, wherein one component of said fastening system is fixedly secured to said strap portion, and the other component of said fastening system is fixedly secured to said second portion.

5. The device of claim 1 wherein said material comprises fabric-covered neoprene rubber.

6. The device of claim 1 wherein said hole is closed by stitching.

7. The device of claim 1 wherein said slot is closed by stitching.

8. The member of claim 1 additionally comprising a pad located on said palmar side of said sleeve at the interface of said intermediate portion and said proximal end portion.

9. A device to be worn on the hand and over a portion of the wrist of a person to prevent or treat carpal tunnel syndrome, said device comprising of a sleeve of elastic material which stretches longitudinally as well as transversely and which includes a palmar side and a dorsal side, a distal end portion, an intermediate portion, and a proximal end portion, said distal end portion including plural respective finger receiving openings, said sleeve having a thumb receiving opening located in said intermediate portion, said proximal end portion of said sleeve having a longitudinal axis and being configured to encircle the wrist of the person when said device is in place with the person's fingers extending through said respective finger openings and with the person's thumb extending through said thumb opening, said dorsal side of said sleeve at said intermediate portion being formed of a blank of said elastic material having a hole therein, said hole having peripheral edge portions spaced apart from each other and being permanently closed by bringing said peripheral edge portions into abutment with each other, whereupon said dorsal portion of said sleeve is biased backwards at a slight angle to said longitudinal axis for extending the person's hand in flexion at said slight angle to said longitudinal axis, said closed hole resisting stretching in said intermediate portion of said sleeve perpendicularly to the direction of said longitudinal axis when said device is worn on the hand, said dorsal side of said sleeve also including a slot therein located adjacent said closed hole, said slot having peripheral edge portions spaced apart from each other, said slot being permanently closed by bringing said peripheral edge portions of said slot into abutment with each other to further the biasing of said dorsal side of said sleeve backwards at said slight angle to said longitudinal axis, said intermediate portion of said sleeve being configured to tightly encircle the person's palm and contiguous dorsal portion of the person's hand to prevent the palm from spreading.

* * * * *